United States Patent [19]

Persson

[11] Patent Number: 5,609,083

[45] Date of Patent: Mar. 11, 1997

[54] METHOD OF AND AN APPARATUS FOR SECTIONING A SPECIMEN

[75] Inventor: Algy Persson, Stockholm, Sweden

[73] Assignee: Glass Ultra Micro Trading Company, Stockholm, Sweden

[21] Appl. No.: 829,067

[22] PCT Filed: Aug. 15, 1990

[86] PCT No.: PCT/SE90/00527

§ 371 Date: Feb. 6, 1992

§ 102(e) Date: Feb. 6, 1992

[87] PCT Pub. No.: WO91/02960

PCT Pub. Date: Mar. 7, 1991

[30] Foreign Application Priority Data

Aug. 16, 1989 [SE] Sweden ................... 8902751

[51] Int. Cl.$^6$ ............... G01N 1/06; B26D 5/20
[52] U.S. Cl. ............... 83/14; 83/73; 83/76.7; 83/915.5
[58] Field of Search ............... 83/13, 915.5, 72, 83/73, 74, 76.7, 703, 14, 713

[56] References Cited

U.S. PATENT DOCUMENTS

| | | | |
|---|---|---|---|
| 3,845,659 | 11/1974 | Wikefeldt et al. | 83/915.5 X |
| 3,937,564 | 2/1976 | Persson | 83/915.5 X |
| 4,532,838 | 8/1985 | Soderkvist | 83/13 |
| 4,991,475 | 2/1991 | Malcok et al. | 83/13 |
| 5,065,657 | 11/1991 | Pfeifer | 83/915.5 X |
| 5,226,335 | 7/1993 | Sitte et al. | 83/915.5 X |

FOREIGN PATENT DOCUMENTS

| | | |
|---|---|---|
| 3127266 | 5/1984 | Germany. |
| 3615715 | 11/1988 | Germany. |
| 349862 | 10/1972 | Sweden. |
| 192431 | 11/1967 | U.S.S.R. ............... 83/915.5 |
| 2130740 | 6/1984 | United Kingdom. |

OTHER PUBLICATIONS

KnifeMaker (Unique damping device gives more usable knife-edge) LKB, 7800 (4 pages), May 1984.

Ultratome III (The Wide-range Ultramicrotome) LKB, 8800 (8 pages), 1973.

LKB Ultratome V, 2088 (6 pages), Jun. 1978.

Ultrotome Ultramicrotome—Basic Principles and Summarized Description of Construction; Borje Hellstrom, Science Tools, The LKB Instrument Journal, pp. 10–16, Aug. 1960.

Primary Examiner—Rinaldi I. Rada
Assistant Examiner—Clark F. Dexter
Attorney, Agent, or Firm—Christie, Parker & Hale, LLP

[57] ABSTRACT

A method and an apparatus for sectioning a specimen (9) by whereas the apparatus is a microtome. The microtome has at least one optical and one additional sensor (35-37) used for generating signals, the value of which is a measure of the sectioning function. At least one essential sectioning parameter, such as the clearance angle of the knife and/or the sectioning speed, is varied. On the basis of the signal values received, the sectioning parameters concerned are set for optimising the sectioning function. The optical sensor (37) senses greyness and/or surface structure of the sections produced. The other sensors are used e.g. for sensing sound (sensor 35) dependent on the sectioning force or work, or stresses in the knife of the microtome (sensor 36) that are dependent on the sectioning force or work.

14 Claims, 1 Drawing Sheet

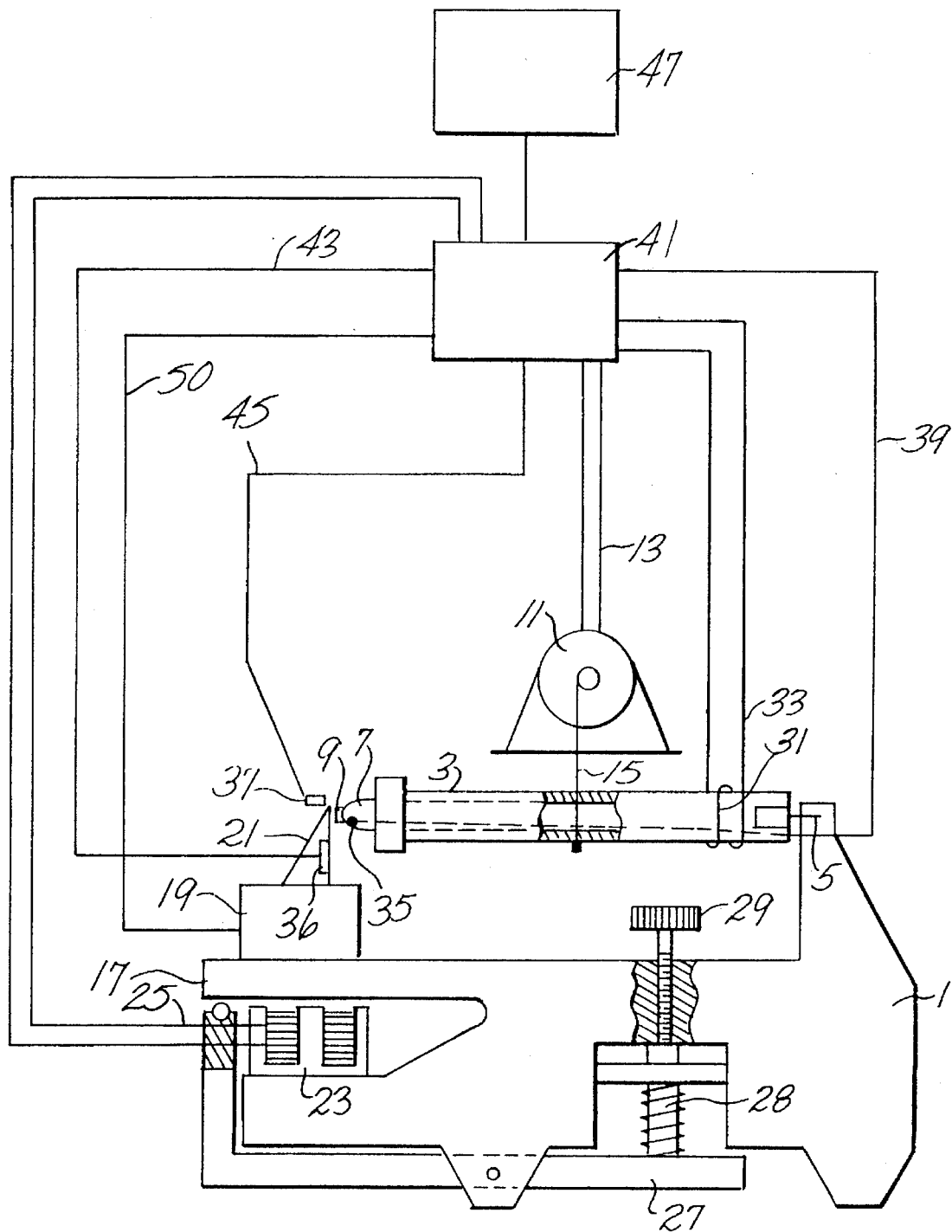

METHOD OF AND AN APPARATUS FOR SECTIONING A SPECIMEN

FIELD OF THE INVENTION

The present invention relates to a method for sectioning a specimen by means of a microtome, at least some of the essential sectioning parameters, such as clearance angle, sectioning speed (or force), type of knife, knife angle and specimen pretreatment, being systematically varied for achieving a sectioning-parameter choice providing an optimised sectioning function. The invention also relates to an apparatus for carrying out the method.

DESCRIPTION OF THE PRIOR ART

In biological and medical investigations and materials testing, use is generally made of microtomes for cutting thin sections of the specimens involved, these sections being examined by light- or electron microscopy.

Specimens that are not immediately sectionable are embedded in suitable media or frozen before sectioning. In the microtomes, the specimen, which is fixed to one end of a vertically movable arm, is generally engaged with a stationary knife. The feed, determining the section thickness, is applied to either the specimen arm or the knife holder.

Detailed information on microtomy and on how a microtome can be designed is given, e.g. in Science Tools, The LKB Instrument Journal, Vol. 7, No. 2, August 1960, pp 10–16, "The Ultrome Ultramicrotome—Basic Principles and Summarized Description of Construction".

Present-day microtomes are handled manually by the operator who tries to evaluate the section quality achieved and intervenes if it is not satisfactory. This evaluation is made with the aid of low-magnifying specimen microscopes. The researcher then makes the conclusive evaluation in his high-resolution light- or electron microscope prior to the actual task of analysing the section contents morphologically and/or analytically. If this latter evaluation shows that the sections are not satisfactory, which is not unusual, sectioning must be repeated with adjusted sectioning parameters. This, of course, means extra work, waste of time and increased costs. Further, particular problems arise if the specimen is not readily available for resectioning.

It has been suggested to vary the knife-angle parameter on the basis of a signal received from a sensor in the form of a load sensor or strain gauge arranged on the knife or the specimen holder. In this manner, the sectioning force can be minimised and so-called chatter eliminated without any examination of the section in an electron microscrope. This, however, provides no overall optimisation of the sectioning function as a whole.

OBJECT OF THE INVENTION

The object of the present invention is to provide improvements in microtomy so as to obviate the above-mentioned problems to a considerable extent while also conferring other advantages.

SUMMARY OF THE INVENTION

According to the invention, the object stated above is achieved by a method and an apparatus having the features stated in the accompanying claims.

The invention is thus based on the insight that, by using a number of sensors associated with the specially interference-protected microtome for detecting a number of selected variables dependent on the sectioning function, it is possible to generate signals the value of which, in a broad sense, is a measure of the sectioning function, i.e. a measure of how free from artefacts or distortions a resulting section is. The variation of the respective signal, when varying one or more sectioning parameters between successive cuts (without any examination of the respective section in a high-resolution microscope), is used as the basis of an optimising sectioning-parameter choice providing the optimum value of the respective signal and, hence, optimised sectioning function, within the limits of the conditions given. When varying the sectioning parameters, the operator may of course consider any preset sectioning-parameter limit values or reference values, like any knowledge gained from experience about suitable or unsuitable relationships between different sectioning-parameter values and signal values. The variation of the sectioning parameter or parameters can be carried out manually, in which case the operator is guided by a presentation of the respective signal values, or automatically by means of a device for evaluating the respective signal values and the means associated therewith for control-signal-dependent variation of the sectioning parameter concerned, the control signals being generated on the basis of the evaluation of the signal-values. Particularly in the latter case, it may be advantageous for the evaluation to use e.g. a microcomputer, especially if signals from several sensors should be weighed together for optimisation purposes.

According to the invention, it is advantageous to use optical detection as a basis for a primary optimising sectioning-parameter variation and thereafter additional detection as a basis for a secondary optimising sectioning-parameter variation, this procedure being repeated, if required, until the desired optimisation of the sectioning function has been achieved.

In optical detection, photometric or ellipsometric sensors are advantageously used, which are suitably applied in association with the microtome means collecting the sections produced. The optical sensors used can be associated with a microscope of conventional type for examining the sections collected.

As to the additional detection, there are several options available. Within the scope of the invention, different types of sensors can thus be used, as will appear from the following examples. Acoustic sensors can be used for detecting sound typical of or dependent on the sectioning force, work or function. An acoustic sensor can e.g. be easily applied to the microtome knife, the knife holder or the specimen holder, preferably integrated in the specimen holder adjacent the specimen held. Load- or vibration-sensitive sensors (basically piezoelectric-type transducers or strain gauges or developments thereof) can easily be applied to the knife, knife holder, specimen or specimen holder, preferably to the knife adjacent its edge. Time-metering sensors can be used for measuring the time required for performing sectioning with a set sectioning force. Acceleration-metering sensors can be used for detecting acceleration changes during the sectioning motion, this making it possible to calculate a measure of the sectioning work. Of course, it is possible to use several of these different types of sensors in one and the same microtome.

According to the invention, it has been found advantageous, as stated above, to set out using optical detection and thus initially vary the sectioning parameters for optimising the optical detection. An additional sectioning-parameter variation is thereafter carried out, using one or more additional detecting functions, while ensuring that the optimised optical detection is not lost. Thus, total optimisation is attained. Within the scope of this optimisation, different aspects can be seen.

According to a first aspect, a signal is generated having a value which is a measure of the sectioning force or work. On the basis hereof, one or more sectioning parameters are set, such that the signal value indicates the minimum sectioning force or work. In fact, it has been found that sectioning involving minimum sectioning force or work generally yields the highest sectioning quality.

According to another aspect, a signal is generated having a value which is a measure of disturbances, such as vibrations or variations of the sectioning speed, appearing during the sectioning function or operation. Vibrations may occur, e.g. when using a knife having too small a knife angle or too weak an edge. It has been found that an optimal sectioning function generally also means a minimum of disturbance.

According to yet another aspect, a signal is generated having a value which is a measure of thickness variations of the section produced or, alternatively, a measure of a thickness deviation of the section produced with respect to a thickness reference value. This aspect of the invention makes it possible to cope with complex problems of the type referred to as "chatter" and "compression".

According to a further aspect, a signal is generated having a value which can be used as a basis for sectioning parameter changes leading to an optimisation or a desired final result of a particular variable, such as section thickness, or a combination of variables, such as section-surface smoothness with regard to sectioning temperature.

It should be emphasised that the invention need not be directed to optimising the sectioning function for obtaining a maximum of information from the sections produced, but may also be directed to optimising the sectioning conditions, such as knife functions and specimen pretreatment. In this context, it should be pointed out that many of the knives currently used, e.g. glass knives, which are sharper and thus less resistant, often have a relatively limited life, which makes it important to obtain "correct" sectioning as soon as possible, i.e. after as few test cuts as possible. Besides, exchanging the knife (for the same type or another type) is a complicated procedure as compared with changing other sectioning parameters of the microtome itself. One possibility of rapidly optimising the pretreatment of a specimen also is of great importance in many cases.

Since the "processes" to be recorded by the sensors often give rise to very small signals, it is essential when using the invention to ensure that the microtome employed has very small background interference or "background noise". Such disturbances may be caused by the presence of friction surfaces, motion-limiting mechanical guides and abutments etc. This can be avoided if use is made of a microtome with a spring-suspended arm, moving-coil-controlled arm motion, thermal feed and electromagnetically-operated resilient retraction of the knife in connection with the return movement of the arm.

According to the invention, one or more sectioning parameters are varied, as earlier mentioned. To this end, use is made of conventional adjusting options in microtomes, e.g. in respect of knife holder, specimen holder and arm drive. However, it is often essential in sectioning that the first contact between the knife and the specimen (so-called approach) is achieved optimally. A stepwise change of one sectioning parameter, e.g. clearance angle, may result in the change of other essential conditions, e.g. the position of the knife edge in relation to the specimen as seen in the direction of feed. This makes it desirable to carry out a new "approach" to ensure e.g. that an excessive amount of specimen material is not cut off in the subsequent sectioning operation.

In an apparatus according to the invention, it is thus preferred to provide special adjusting systems (in addition to the conventional ones) which allow highly reproducible, limited stepwise optimising adjustments of the sectioning parameters concerned in opposite directions. These adjustments should not give rise to any reciprocal influence, i.e. should not necessitate a new "approach". Such adjusting systems may be based e.g. on magnetostrictive, piezoelectric or similar components. These components can be made very robust, so that no weak elements are integrated in the microtome.

The invention will be described in more detail hereinafter in an embodiment with reference to the accompanying drawing.

BRIEF DESCRIPTION OF THE DRAWING

The schematic FIGURE illustrates the basic design of an apparatus according to the invention including a microtome, the main components of which are seen from the side.

DESCRIPTION OF AN INVENTIVE EMBODIMENT

The apparatus as shown in the drawing is designed setting out from an ultramicrotome known per se, comprising a foundation 1; a specimen arm 3 which is suspended at its rear end from the foundation 1 by means of leaf springs 5 so as to be pivotable downwards and up again in the plane of the drawing, and which has at its front end a specimen holder 7 for a specimen 9 to be cut; an electronically controlled moving-coil unit 11 with associated control-signal lines 13 and a connecting string 15 connected to the specimen arm for controlling the downward-upward motion of the specimen arm 3; a knife holder 19 provided with a knife 21 and arranged on a platform 17 projecting freely from the foundation 1, the position of the knife being adjustable for setting, inter alia, the desired clearance angle set by means of knife holder 19; an electromagnet 23 arranged on the foundation 1 underneath the platform 17 and provided with control-signal lines 25 for controlled excitation of the electromagnet in order to attract the platform 17, thus retracting the knife 21 in a controlled manner in connection with the upward return stroke of the specimen arm after a downward cutting motion; spring-biased, manually operable link means 27, 28, 29 for manually acting on the platform 17 and hence the position of the knife 21; and a heating coil 31 with associated thermal-feed lines 33 for the specimen arm 3. Knife holder 19 is shown schematically because knife holders capable of adjusting the setting of the clearance angle and varying the type of knife are well known in the art.

According to the invention, the microtome is provided with three sensors, namely a sound-detecting sensor 35, a force- or stress-detecting sensor 36 and an optical sensor 37.

The sound-detecting sensor 35 is disposed on the specimen holder 7 as close to the specimen 9 as possible, and its connecting lines 39 pass through the specimen arm 3 and on to an evaluation unit 41. As is readily understood, the sensor 35 may simply consist of a miniature microphone and, in the simplest case, can detect the intensity of the sound dependent on the sectioning work.

The stress-detecting sensor 36 may be of the strain gauge-type and be fixed on one side face of the knife 21, suitably with its main axis substantially vertical. Thus, this sensor can detect e.g. flexions appearing in the knife on account of the sectioning work performed (at 7). The sensor can also detect vibrations in the knife. The connecting lines 43 of the sensor 36 are also connected to the unit 41.

The optical sensor 37 is disposed above the conventional liquid bath (not shown) provided on the knife holder 19 for receiving the sections produced. Advantageously, the sensor 37 is arranged on optical equipment, such as a microscope of conventional type, which is normally used in connection with a microtome for initially checking the sections produced. The sensor 37 may be e.g. a so-called array sensor or CCD sensor for greyness detection. The sensor is also connected through lines 45 to the evaluation unit 41.

The evaluation unit 41 is thus supplied with the signals generated by the sensors 35, 36 and 37, evaluates these signals and emits a signal, representing the result of the evaluation, to a display unit 47 where the value or values of the last-mentioned signal is presented in a suitable manner, e.g. in the form of a bar chart, in which the height of the bar or bars is a measure of the sectioning function.

The sensors can be used separately or in combination. In the latter case, the evaluation unit 41 can be adapted to weigh together the two sensor signals according to predetermined or empirically established rules, such that a single signal value is displayed by the unit 47. As readily appreciated, the unit 41 may comprise e.g. a suitably programmed microcomputer. The unit 41 may, as easily understood, also be adapted to automatically vary, on the basis of the signal values received and according to a given program, different sectioning parameters by supplying signals to the corresponding adjusting system, as previously mentioned.

As illustrated in the drawing, unit 41 is coupled a) to moving coil unit 11 by control-signal lines 13 to set the value of the sectioning speed; b) the control-signal lines 25 to electromagnet 23 to control the retraction of knife 21 in connection with the upward return stroke of the specimen arm; c) by thermal-feed lines 33 to heating coil 31 to control the temperature of the specimen arm; and d) by a control-signal line 50 to knife holder 19 to adjust the knife position, including inter alia the clearance angle.

One example of how the apparatus described above can be used will now be given as a number of method steps for systematically varying one or more sectioning parameters:

a) using a selected knife and a first selected value of the clearance angle (set by means of the knife holder 19 by means well known in the art) and a first selected value of the sectioning speed (set by means of the moving-coil unit 11), the specimen is cut at least once, a pertaining first signal value primarily based on the optical detection being recorded on the unit 47;

b) the value of one of the sectioning parameters clearance angle and sectioning speed is changed one step in a first direction, whereupon the specimen is cut at least once and a pertaining second signal value is recorded;

c) if, in terms of optimisation, the second signal value is superior to the first signal value, the value of said one sectioning parameter is changed one step in the same direction at least once more, whereupon the specimen is cut at least once and a pertaining third signal value is recorded;

d) if, in terms of optimisation, the second signal value is inferior to the first signal value, the value of said one sectioning parameter is changed one step in the opposite direction, counting from the first selected value, whereupon the specimen is cut at least once and a pertaining fourth signal value is recorded;

e) if, in terms of optimisation, the fourth signal value is superior to the first signal value, the value of said one sectioning parameter is optionally changed one step in said opposite direction at least once more, whereupon the specimen is cut at least once and a pertaining fifth signal value is recorded;

f) said one sectioning parameter is given the value which has been found to give the best of the above-mentioned signal values;

g) the value of the other of the sectioning parameters clearance angle and sectioning speed is changed one step in a first direction, whereupon the specimen is cut at least once and a pertaining sixth signal value is recorded;

h) if, in terms of optimisation, the sixth signal value is superior to the best previous signal value corresponding to the value of said one sectioning parameter according to step f), the value of said other sectioning parameter is changed one step in the same direction at least once more, whereupon the specimen is cut at least once and a pertaining seventh signal value is recorded;

i) if, in terms of optimisation, the sixth signal value is inferior to the best previous signal value corresponding to the value of said one sectioning parameter according to step f), the value of said other sectioning parameter is changed one step in the opposite direction, counting from the first selected value, whereupon the specimen is cut at least once and a pertaining eighth signal value is recorded;

j) if, in terms of optimisation, the eighth signal value is superior to said best previous signal value, the value of said other sectioning parameter is optionally changed one step in said opposite direction at least once more, whereupon the specimen is cut at least once and a pertaining ninth signal value is recorded;

k) said other sectioning parameter is given the value which, in terms of optimisation, has been found to give the best signal value.

l) the intended sectioning is performed, unless it is desirable to optimise also the knife angle, in which case:

m) one or more knife exchanges are made each knife having a different angle, the other sectioning parameters being adjusted for each new knife angle according to step k) and, for each new knife angle, the pertaining signal value being recorded on the unit 47. For the final sectioning, that knife is of course selected which has an angle that has been found to give the best signal value on the unit 47.

Steps a)–l) are preferably carried out while maintaining the normal sectioning interval in view of the thermal feed set. A typical sectioning interval may be 4 sec. This means that steps a)–l) can be carried out in a very short time, generally less than 1 min. Compared with prior-art optimising methods, this is a highly time-saving technique.

It will be appreciated that, to the above-mentioned end, use is advantageously made of a microtome where the knife holder 19 is so modified that also the clearance angle can be changed stepwise by an electronic control signal.

As is also readily understood, the electronic control signals can be controlled entirely manually by the operator or semi-automatically, in which case the operator merely gives an overall command based on the display on the unit 47, or fully automatically using a suitably modified unit 41 which emits the electronic control signals concerned.

I claim:

1. A method for sectioning a specimen with a microtome, the microtome having a knife to produce sections with desired characteristics by varying one or more essential sectioning parameters, wherein the essential sectioning parameters are selected from a group consisting of type of knife, knife angle, clearance angle, sectioning speed, specimen pretreatment and combinations thereof, to thereby select a sectioning-parameter or combination of sectioning-parameters which provides an optimized sectioning function, comprising the steps of sectioning making said successive sectioning cuts through the specimen using a microtome; generating at least one signal during a sectioning cut which is a measure of the sectioning function by means of at least two sensors associated with the microtome of which a first one of the sensors is an optical sensor means for optical detection of a surface characteristic of the section produced, and a second one of the sensors is a sensor means for detecting sectioning work; and varying, on the basis of the at least one signal, at least one of said essential sectioning parameters so as to optimize the sectioning function to an optimal predetermined sectioning parameter value, without examination of successive sections in a high-resolution microscope.

2. The method as claimed in claim 1, characterized by using the optical sensor means for detection as a basis for a primary optimizing sectioning-parameter variation and thereafter using said other sensor means for detection as a basis for a secondary optimizing sectioning-parameter variation as required, until the desired optimization of the sectioning function has been achieved.

3. The method as claimed in claims 1 or 2, wherein the other sensor means for detecting sectioning work detects sound dependent on the sectioning work.

4. The method as claimed in claim 1, additionally comprising a third sensor which is a sensor means for detecting stresses dependent on the flexions of the knife.

5. The method as claimed in claim 1, wherein the step of varying at least one of the essential sectioning parameters includes automatically varying one or both of the clearance angle and the sectioning speed according to a predetermined program.

6. The method as claimed in claim 1 wherein the surface characteristic is greyness.

7. The method as claimed in claim 1 wherein the surface characteristic is surface structure.

8. An apparatus for performing a sectioning function on a specimen, said apparatus having a knife for cutting the specimen, while exerting sectioning force and performing sectioning work, and varying means for varying a number of essential sectioning parameters, characterized in that said apparatus comprises a plurality of sensors including an optical sensor means for detecting a surface characteristic of sections produced, each sensor emitting, during sectioning, a signal dependent on at least one characteristic of the sectioning function, and the varying means includes means for receiving the sensor signals emitted and for providing a measure of the sectioning function on the basis of the signals emitted.

9. The apparatus as claimed in claim 8, wherein the plurality of sensors further includes a sensor means for detecting at least one of the following variables: sound dependent on the sectioning work; stresses in the knife dependent upon flexions and vibrations in the knife.

10. The apparatus as claimed in claim 8 or 9, wherein the varying means generates electronic control signals, on the basis of said measure of the sectioning function, to optimize the sectioning function.

11. The apparatus as claimed in claim 8 wherein the surface characteristic is greyness.

12. The apparatus as claimed in claim 8 wherein the surface characteristic is surface structure.

13. The apparatus as claimed in claim 8, in which the varying means comprises means for varying the sectioning speed.

14. The apparatus as claimed in claim 8, in which the varying means comprises means for varying the clearance angle.

* * * * *